Figure 1:
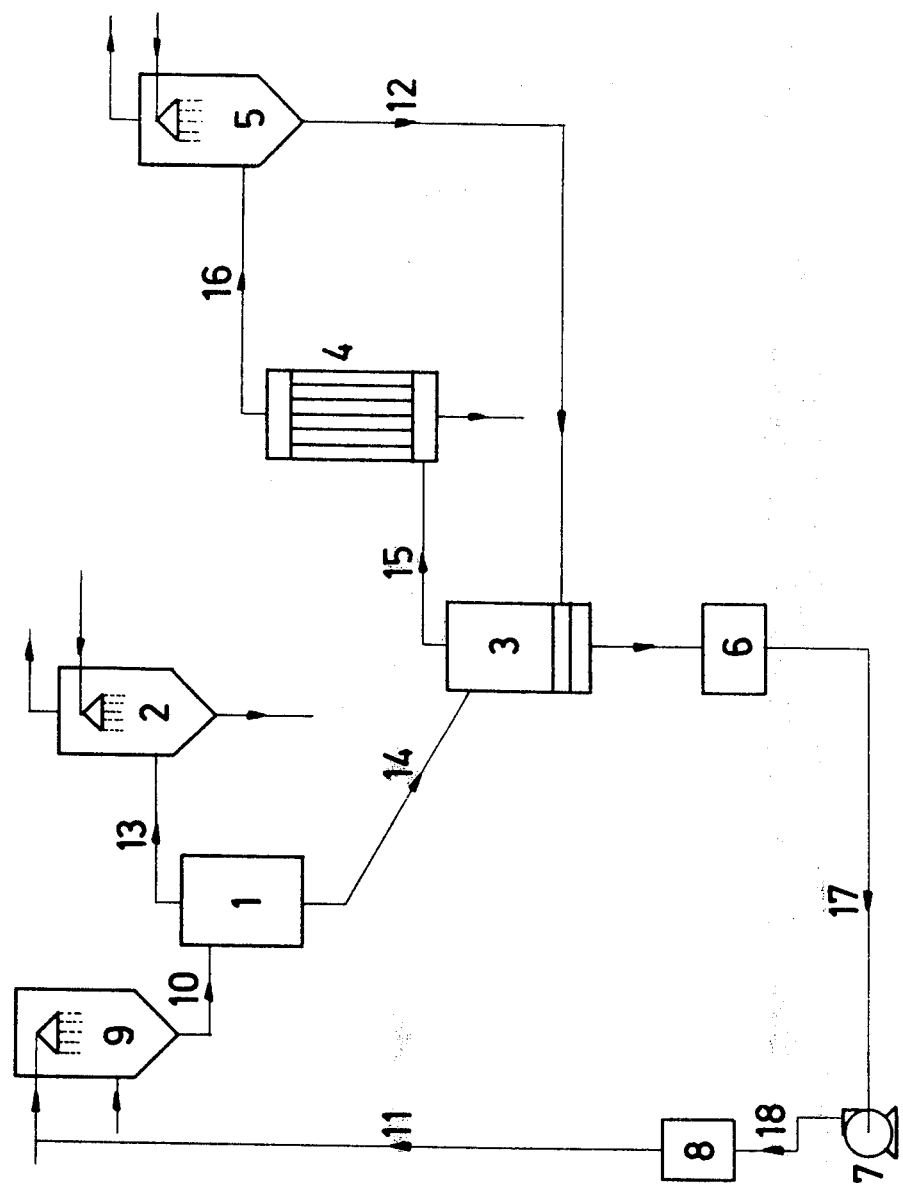

United States Patent [19]

Lietard et al.

[11] 4,009,186
[45] Feb. 22, 1977

[54] PROCESS FOR THE PREPARATION OF MALEIC ANHYDRIDE FROM MALEIC ACID IN THE PRESENCE OF SULFOLANE

[75] Inventors: Jean-Marie Lietard, Gent; Guido Matthijs, Mariakerke, both of Belgium

[73] Assignee: U. C. B., Societe Anonyme, Brussels, Belgium

[22] Filed: July 10, 1975

[21] Appl. No.: 594,672

[30] Foreign Application Priority Data

July 12, 1974 United Kingdom ............. 30938/74

[52] U.S. Cl. ........................................ 260/346.8 M
[51] Int. Cl.$^2$ ........................................ C07D 307/60
[58] Field of Search ............................. 260/346.8 A

[56] References Cited

UNITED STATES PATENTS 3,891,680  6/1975  Katsumoto et al. ........ 260/346.8 M

*Primary Examiner*—Natalie Trousof
*Assistant Examiner*—Bernard Dentz
*Attorney, Agent, or Firm*—Wenderoth, Lind & Ponack

[57] ABSTRACT

Process for the preparation of maleic anhydride from maleic acid by heating the latter in the presence of an organic solvent, which comprises using sulfolane as the organic solvent.

11 Claims, 2 Drawing Figures

PROCESS FOR THE PREPARATION OF MALEIC ANHYDRIDE FROM MALEIC ACID IN THE PRESENCE OF SULFOLANE

The present invention is concerned with a process for the preparation of maleic anhydride from maleic acid in the presence of an auxiliary solvent; the process being characterized in that use is made of sulfolane as the auxiliary solvent.

In the context of the invention, by "maleic acid", there is to be understood maleic acid as such i.e. solid or molten, a mixture of maleic acid with maleic anhydride or aqueous maleic acid.

At the present time, it is already known to use auxiliary solvents for the dehydration of maleic acid which is formed in industrial installations producing maleic anhydride by catalytic oxidation of aliphatic or aromatic hydrocarbons in the gas phase with molecular oxygen or gaseous mixtures containing the latter. The purpose of using an auxiliary solvent is to produce operating conditions such that the conversion of maleic acid to fumaric acid is reduced to the minimum and/or that the elimination of incrustations which are formed on the walls of the dehydration apparatus is facilitated and/or that the formation of tarry products is avoided.

Thus, according to French Pat. No. 1,317,308, the dehydration of an aqueous solution of maleic acid is effected in the presence of a solvent boiling between 160° and 200° C., this solvent consisting of an aliphatic ester or of an aliphatic or alicyclic ketone.

In U.S. Pat. No. 2,250,091, in which the dehydration is first carried out under pressure and between 160° C. and the temperature of decomposition of maleic anhydride and the gas mixture produced is then expanded in order to separate the water, use is made of an auxiliary solvent boiling above 240° C., namely heavy hydrocarbons, ethers, esters, organic acids, organic acid anhydrides, fused salts or sodium bisulfate.

In U.S. Pat. No. 2,166,556, two types of solvent are used at the same time, namely:
 a. a solvent boiling above 200° C., i.e. esters, optionally chlorinated or nitrated aromatic hydrocarbons, aromatic ethers or aromatic acids; and
 b. a solvent boiling below 130° C., such as the lower chlorinated aliphatic hydrocarbons, aliphatic ethers and light aliphatic, cycloaliphatic and aromatic hydrocarbons.

In U.S. Pat. No. 2,832,802, an aqueous solution of maleic acid is atomized at 170° C. into a hydrocarbon boiling at 180°–400° C.

In French Pat. No. 1,125,014, which relates to a process of separating and purifying anhydrides of organic diacids, particularly maleic anhydride, the anhydride is dissolved in a solvent which is immiscible with water (dibutyl phthalate or the like) and the anhydride solution is distilled in the presence of a saturated aliphatic hydrocarbon boiling at a temperature above 190° C.

In French Pat. No. 1,321,417, maleic acid is heated to about 160° C. with an azeotropic agent, such as xylene or anisol, optionally in the presence of a mass of maleic anhydride.

In Dutch patent application No. 7,308,490, use is made of an organic liquid having a boiling point exceeding by at least 100° C. the boiling point of maleic anhydride, for example a residue from the production of organic acids or acid anhydrides.

To sum up, it can, on the one hand, be seen that none of the above-mentioned Patents describes the use of sulfolane as an auxiliary solvent in the dehydration of maleic acid to maleic anhydride. On the other hand, all these patents have in common the use of auxiliary solvents which are insoluble in water. Unlike the solvents mentioned, sulfolane, which is used as the solvent according to the present invention, is water soluble. Its boiling point at atmospheric pressure is 287.3° C. In the anhydrous state, its melting point is 28.68° C.; however, the commercial product is in the form of a liquid containing about 2% of water and having a density of 1.2614 at 30° C.

Sulfolane has already been proposed as an extraction solvent for separating a vaporizable liquid mixture of organic components, which components may, for example, be mixtures of organic mono- or polycarboxylic acids (see U.S. Pat. Nos. 2,360,859 and 2,360,861). In the process of the present invention, it is however not proposed to separate selectively an acid from a mixture of acids by extraction with sulfolane but to convert the maleic acid as completely as possible into maleic anhydride, while forming the smallest possible amount of fumaric acid in the course of the conversion. This also explains why maleic acid (or its anhydride) is not mentioned among the organic acids which can be separated by the process of these two U.S. Patent Specifications.

Furthermore, according to the present invention, we have, surprisingly, discovered that sulfolane considerably accelerates the dehydration of maleic acid to maleic anhydride without significantly increasing the formation of fumaric acid; as will be seen in the Examples, the use of sulfolane as auxiliary solvent makes it possible practically to double the production capacity of equipment for converting maleic acid into maleic anhydride, thus providing a considerable industrial advantage.

Thus, the present invention provides a process for the preparation of maleic anhydride from maleic acid by heating maleic acid in the presence of sulfolane.

The maleic acid used as starting material is either substantially pure solid or molten maleic acid, or a mixture of maleic acid and maleic anhydride or simply aqueous maleic acid.

The use of sulfolane as auxiliary solvent in the process of the present invention provides a series of advantages which may be summarized as follows:
 a. sulfolane has remarkable dissolving power for maleic acid, fumaric acid and maleic anhydride and for the resins and tars which are formed in the course of the dehydration process;
 b. it lowers the liquefaction temperature of the residues;
 c. because of its high boiling point, the losses of sulfolane in the system are zero or negligible;
 d. since the boiling point of sulfolane is almost 100° C. higher than that of maleic anhydride, there is no problem in separating these two substances by distillation;
 e. sulfolane is non-inflammable;
 f. sulfolane is non-corrosive, which makes it possible to use ordinary construction materials for the apparatus, for example ordinary carbon steel;
 g. sulfolane is non-toxic, which is an advantage over the majority of solvents proposed hitherto;
 h. it is completely inert to maleic acid and maleic anhydride, unlike certain solvents, such as esters, which can react maleic acid and/or anhydride by transesterification;

i. it prevents the formation of incrustations on the heat exchange surfaces, which is the main problem encountered in the dehydration of maleic acid, because it necessitates the shut-down of production in order to clean the surfaces affected;

j. it considerably accelerates the speed of dehydration of maleic acid into the corresponding anhydride;

k. finally, and above all, its solubility in water makes it possible to use it in continuous processes (without stopping production for cleaning purposes) in which part of the mixture undergoing dehydration (containing maleic acid, fumaric acid, maleic anhydride, resins, tars, residues of oxidation catalyst and the like) is continuously withdrawn for treatment with water and then filtered, thus giving a filtrate (aqueous solution of maleic acid) which is returned to the concentration stage, while the cake composed of water insoluble residues (fumaric acid, resins, tars, catalyst and the like) is removed from the system. Since sulfolane is water-soluble, it accompanies the aqueous extraction filtrate containing maleic acid and it is thus directly recycled, without having to undergo distillation. Sulfolane is, therefore, remarkably convenient for use in continuous processes for the dehydration of maleic acid to maleic anhydride which are described, for example, in Belgian Pat. No. 745,029 and in British Patent Specification No. 1,424,727.

l. because of the advantageous properties of sulfolane, it can also be used in all the processes mentioned above to replace the high boiling point solvents which are used therein, with a view to preventing incrustations, combating the formation of tars, fluidizing the residues and the like.

The amount of sulfolane added depends essentially on the dehydration process used. By means of a few preliminary tests, it is very easy to determine, for a given process, the most suitable amount of sulfolane. As a rule, the amount of sulfolane to be added will be at least 2% by weight, referred to the amount of maleic acid to be dehydrated into maleic anhydride, advantageously at least 5% and preferably at least 10%. The upper limit of the amount of sulfolane to be added for the dehydration of maleic acid to maleic anhydride is governed not by technical but solely by economic considerations.

In the process according to the invention for the preparation of maleic anhydride from maleic acid by heating the latter in the presence of sulfolane, heating is effected at a temperature of about 100° to about 210° C., preferably about 120° to about 200° C., under a pressure of about 30 to about 760 mm Hg, preferably about 60 to about 200 mm Hg.

Examples 1 to 3 show the advantageous effect of sulfolane on the dissolution of the distillation residues, the facility of separation by distillation of the obtained maleic anhydride from the sulfolane and the advantageous effect of sulfolane on the incrustations, whereas Examples 4 to 7 are non limiting examples of the use of sulfolane in processes for the manufacture of maleic anhydride from maleic acid.

EXAMPLE 1

This Example shows the excellent power of sulfolane to dissolve and liquefy the distillation residue which is formed in industrial installations for converting maleic acid into maleic anhydride. This residue is that withdrawn from industrial dehydration plants when the latter are clogged to such an extent that it is no longer possible to continue the operation; the operation of the apparatus is then interrupted and the apparatus cleaned.

The composition of this residue is, for example, as follows:
  maleic anhydride — 26% by weight
  maleic acid — 25.2% by weight
  fumaric acid + resins — 48.8% by weight
appearance: very hard substance, colour dark brown, impossible to remelt.

When 10% by weight of sulfolane is added to this residue in a test tube and the mixture heated to 120° C., there is obtained a molten mixture of medium viscosity which does not stick to the walls of the glass tube. On cooling to about 50° C., it solidifies but is easily remelted by heating.

EXAMPLE 2

This Example shows the excellent results obtained when crude maleic anhydride is distilled in order to separate it from sulfolane.

The crude anhydride used contains about 98% of maleic anhydride and about 2% of maleic acid (by weight).

200 g. of sulfolane are first introduced into a circulation still with a capacity of about 1 kg. of maleic anhydride, the still being provided with a 10-plate Oldershow column, whereupon 80 kg. of crude maleic anhydride, i.e. 80 times the volume of the still are added in the course of 200 hours, using the following operating conditions:
  pressure: vacuum of about 120 mm. Hg. (b.p. of anhydride: about 140° C.)
  reflux rate: 50/50
  working rate: about 400 g. of maleic anhydride per hour.

Every 4 hours, a sample is taken to determine the APHA coloration. The APHA coloration, which after 4 hours is 150, decreases progressively so that in the 200th hour of operation it is only 15 APHA. However, since the formation of residue increases in the course of this period, it was expected that the coloration will increase and not decrease. It is concluded therefrom that the sulfolane retains the chromogenic substances in solution. In the course of this experiment, the melting point of the anhydride separated was periodically measured; it is always higher than 52.4° C. Only traces of maleic acid are detected and the sulfolane content, measured by gas phase chromatography of the resulting product, is at most 25 ppm.

When the maleic anhydride thus obtained is stabilized by redistillation, sulfolane can no longer be detected by gas phase chromatography, while the APHA coloration has fallen to less than 10.

EXAMPLE 3

Effect of sulfolane on incrustations.

Test tubes of large dimensions are used in which a threaded stainless steel rod with a diameter of 10 mm. is mounted axially with the aid of a rubber stopper. The same residue as was used in Example 1 is introduced into each test tube and variable amounts of sulfolane are added. Each test tube is then heated to 120° C. under thermostatic control. The threaded rod is then regularly withdrawn from the tube and allowed to drain. After about 100 minutes, a stationary condition is reached and the increase of weight, referred to the unit of length submerged, is then measured. The results obtained are given in the following Table:

TABLE

| % by weight of sulfolane added | deposition of residue in g./cm. of rod |
|---|---|
| 1 | 0.72 |
| 2 | 0.54 |
| 5 | 0.36 |
| 10 | 0.29 |
| 20 | 0.21 |

EXAMPLE 4

Effects of sulfolane on the speed of dehydration of maleic acid.

This Example shows the advantage of adding sulfolane in the azeotropic entrainment of water by xylene in accordance with the already mentioned French Pat. No. 1,321,417.

Three moles of maleic anhydride, to which three moles of maleic acid are added, are melted by means of an electric mantle in a two-liter glass flask provided with an anchor type agitator and a condenser-decanter arrangement.

The mixture is heated to 135° C., 100 ml. of o-xylene are introduced and the mixture is distilled. The heteroazeotrope is collected, while measuring the amount of water formed as a function of time, the decanted organic phase being recycled. The following Table shows that the presence of sulfolane increases the speed of dehydration by a factor of 2.

| Test No. | 1 | 2 |
|---|---|---|
| Temperature in ° C. | 140–150 | 140–150 |
| Sulfolane (% by weight) | 0 | 10 |
| Speed of dehydration (moles of $H_2O$ per hour) | 1.42 | 2.83 |
| Dehydration yield at 160° C. after 1 hour in % | 35 | 70 |

The following three Examples illustrate the process of the present invention applied to known industrial processes:

EXAMPLE 5

In an industrial installation for the production of maleic anhydride from maleic acid, in which a still dehydrator having a working volume of 3 m³ is connected to a dephlegmator on which is mounted a condenser kept at 80° C., there are introduced, per hour, into the still-dehydrator, on the one hand, 500 kg. of crude maleic anhydride coming from the condensers downstream of the reactor for the catalytic oxidation of benzene to maleic anhydride and, on the other hand, 600 kg. of molten maleic acid ($T = 135°$ C.) coming from a thin layer evaporator. The operating conditions of the still-dehydrator are originally: temperature about 135° C. and pressure about 100 mm. Hg. Nevertheless, in order to maintain the same production rate per hour, it is necessary for the temperature to be progressively increased and for the pressure to be progressively lowered, because of the increasing clogging of the heating surfaces. When it is necessary to interrupt the operation, the temperature is 145° C. and the pressure is 60 mm. Hg.

In the absence of sulfolane, the installation described above thus produced 85 tons of maleic anhydride in 90 hours. On the other hand, if 80 kg. of sulfolane (2.5% by weight referred to the total charge) are initially added to the still-dehydrator while the other operating conditions remain the same, an output of 175 tonnes of maleic anhydride in 185 hours is achieved.

Surprisingly, despite the fact that the amount of resinous products is doubled when sulfolane is used, because practically twice the amount of maleic anhydride is produced, the heat exchange surfaces of the still-dehydrator are less incrusted by resinous products, since the latter are solubilized by the sulfolane. According to the present invention, one cleaning operation out of two is thus saved, thereby correspondingly increasing the production capacity of the installation.

EXAMPLE 6

This Example describes the use of sulfolane in the continuous process of dehydration of maleic acid to maleic anhydride according to Belgian Pat. No. 745,029.

FIG. 1 of the accompanying drawings shows an installation designed for treating 1000 moles of maleic acid per hour (116 kg. per hour). This maleic acid, obtained by washing with water in a washer 9 the gas passing out of the reactor for the catalytic oxidation of benzene (not shown in the drawings), is in the form of an aqueous solution containing 450 grams of acid per liter.

According to the present invention, 11.6 kg. of sulfolane are added to the washer 9 so that the weight ratio of maleic acid to sulfolane is 10 : 1 in the installation. Since the sulfolane circulates in a closed circuit, the amount thereof remains constant. The aqueous solution of maleic acid and sulfolane is passed through a pipe 10 to the evaporator 1, in which it is heated to a temperature of 135° C. at a pressure of 550 mm.Hg.

The vaporized water escapes through a pipe 13 and is condensed in a barometric washer 2 connected to a vacuum source (not shown), while the remaining mixture of maleic acid and sulfolane, which now contains only about 1% by weight of water, passes out at the bottom of the evaporator 1 at a temperature of 135° C. and is passed through a pipe 14 to the top of a second thin layer evaporator 3.

In the evaporator 3, in which the molten maleic acid is progressively brought to a temperature of 200° C. under a pressure of 150 mm. Hg., the maleic acid is converted to the extent of 90% by weight into maleic anhydride in the form of a vaorized mixture of maleic anhydride and water, while the remaining 10% of unconverted maleic acid flows, together with the sulfolane, in the form of a liquid phase to the bottom of evaporator 3.

The vapors of water and maleic anhydride are passed through a pipe 15 into a condenser 4 operating at a temperature of 80° C. The maleic anhydride obtained as the product of the process is collected in a liquid state at the bottom of the condenser 4 at the rate of 900 moles per hour; its maleic anhydride content is 99.5%, its fumaric acid content is practically zero and its content of other impurities is 0.4% by weight. The maleic anhydride obtained in this manner is passed to a distillation column (not shown) for the removal of the last traces of impurities and for stabilization.

The water vapor which escapes at the top of the condenser 4 is passed through a pipe 16 to a barometric washer 5 connected to a vacuum source (not shown) in order to recover traces of maleic anhydride entrained by the water vapor; the dilute aqueous solution of maleic acid is recycled (see below).

The liquid phase of maleic acid and sulfolane, which flows at the bottom part of the evaporator 3 and contains, in solution, all the impurities accumulated in the installation, is mixed with the dilute maleic acid solution coming from the barometric washer 5 through the pipe 12 and is collected in a receiver 6. This receiver operates at a temperature of 30° C. and under a pressure of from 40 to 300 mm.Hg. As the result of this addition of a dilute aqueous solution, the fumaric acid and resins are precipitated and this suspension is withdrawn from 6 through a pipe 17 by means of a pump 7 and is delivered through a pipe 18 to a filter 8. The filter 8 is designed so as not to interrupt the continuous operation of the installation (double filtration circuit, now shown).

The filter cake, which contains the impurities accumulated in the system (these include fumaric acid and various impurities originating from secondary reactions on the catalyst), is eliminated from the installation, while the filtrate, composed of an aqueous solution of maleic acid and sulfolane, leaves the filter through pipe 11 and is returned entirely to washer 9.

In comparison with the process of Belgian Pat. No. 745,029, the process of the present invention offers the advantage of completely eliminating the danger of obstruction of the installation at the critical points, particularly at the bottom of the evaporator 1, in pipe 14 connecting evaporators 1 and 3 and at the bottom of evaporator 3. Furthermore, because of the dissolving properties of sulfolane, the heat exchange surfaces of evaporators 1 and 3 remain clean.

It should be noted that there may be a slight loss of sulfolane in the filter cake. This slight loss can be made good by the suitable introduction of sulfolane at any point in the installation, preferably in washer 9.

EXAMPLE 7

Figure 2:
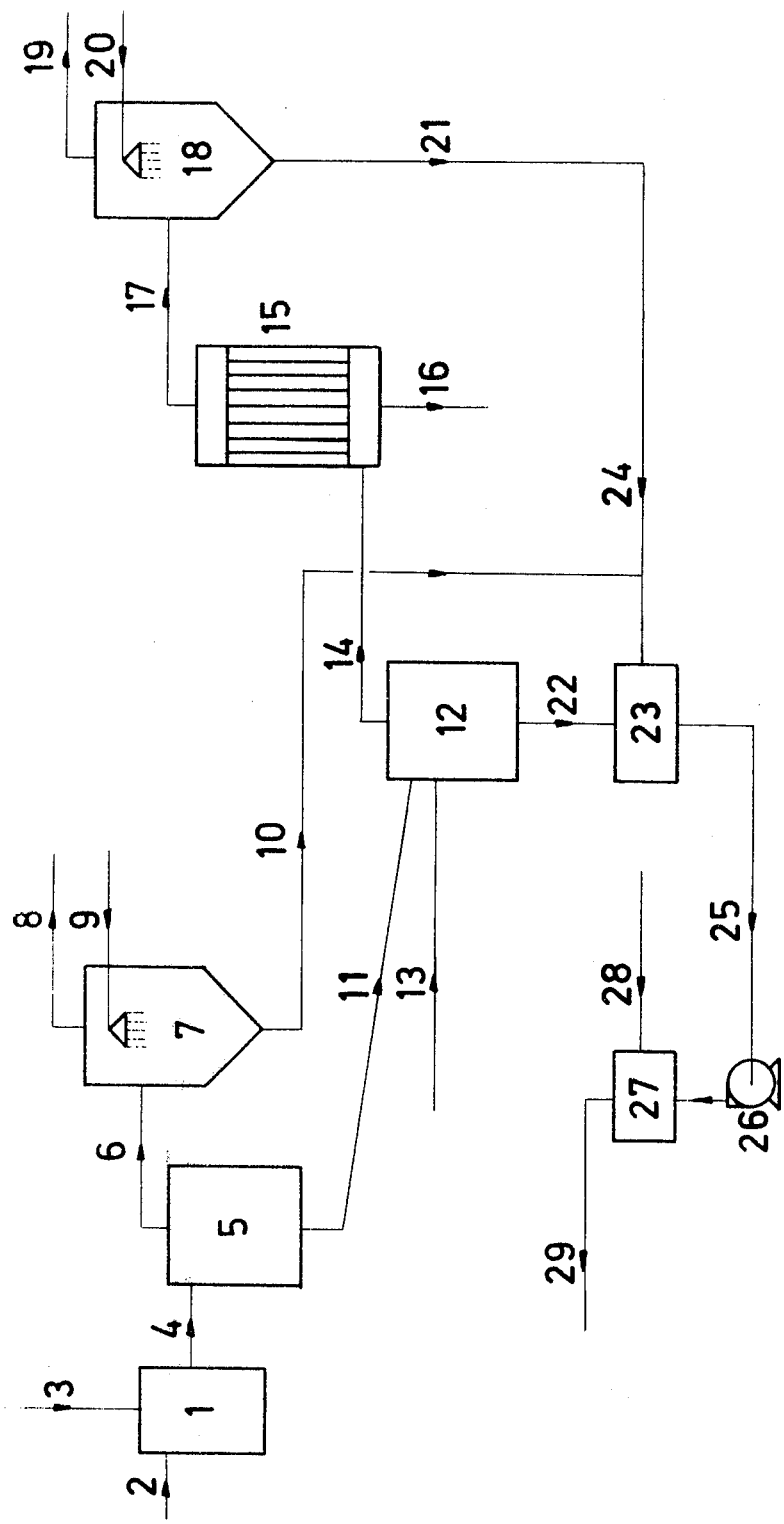

This Example illustrates the application of the process of the present invention to the process of British Patent Specification No. 1,424,742, the installation of which is shown in FIG. 2 of the accompanying drawings.

A benzene oxidation reactor (not shown) produces 2000 moles of maleic anhydride per hour, 1000 moles per hour of which are condensed by cooling the gases in the condensers (not shown) and 1000 moles per hour are recovered in the form of an aqueous solution of maleic acid in the washer 1. At the moment when the installation is put into operation, sulfolane is added, according to the present invention, in an amount such that the concentration in the washing loop amounts to 45 grams per liter.

This washer is fed at 3 by a recycled aqueous solution coming from barometric washers 7 and 18. This aqueous solution contains about 75 moles per hour of recovered maleic acid and also 125 moles per hour of maleic acid recovered from the drain circuit 22, 23, 25, 26, 27, 29 and 3 (which, in addition, contains sulfolane).

As shown in FIG. 2, the aqueous solution coming from the barometric washers 7 and 18 serves to dissolve this drained product; after filtration, this solution, which contains 200 moles per hour of maleic acid, is recycled to the washer 1 through the pipes 29 and 3.

The evaporator 5 is thus fed with a concentrated aqueous solution, containing 450 g. of maleic acid per liter and 45 g. of sulfolane per liter, at a rate of 1200 moles of maleic acid per hour (1000 moles per hour coming from the washing of the gases leaving the maleic anhydride condensers and 200 moles of maleic acid per hour (125+75) coming from recycling at 3).

The water vaporized from the aqueous solution of maleic acid at a temperature of 135° C. and a pressure of 500 mm.Hg. in the evaporator 5 escapes through pipe 6 and is condensed in barometric washer 7, while the mixture of maleic acid and sulfolane now containing only 1% by weight of water passes out at the bottom of the evaporator at a temperature of 135° C. and is passed through pipe 11 to the still-dehydrator 12.

The latter, which also receives the 1000 moles per hour of maleic anhydride coming from the condensers (not shown) through pipe 13, contains a weight of reaction mixture corresponding to four times the hourly amount by weight of maleic anhydride produced by the reactor, i.e. 8000 moles, calculated as maleic anhydride. The still-dehydrator operates at a pressure of 135 mm.Hg. and at a temperature of 135° C. At the commencement of the operation of the installation, 43 kg. of sulfolane are added to the still-dehydrator so that, in the latter, the concentration of sulfolane will be 5% by weight, referred to the total weight of maleic acid plus anhydride.

The condenser 15 condenses, at a temperature of 80° C., 2000 moles per hour of pure maleic anhydride, from which must be deducted the loss of the drain circuit, which at most amounts to 1.5% by weight. The pure maleic anhydride obtained as product of the process is collected in the liquid state at the bottom of the condenser 15 through the pipe 16; its maleic anhydride content is 99.5% by weight, its fumaric acid content is practically zero and its content of other impurities is 0.4% by weight. The maleic anhydride obtained in this manner is passed to a distillation column (not shown) for removal of the last traces of impurities and for stabilization. The water vapour which escapes at the top of condenser 15 is passed through pipe 17 to barometric washer 18 connected to a vacuum source (not shown) in order to recover traces of maleic anhydride entrained by the water vapour; the aqueous solution of maleic acid obtained is either recycled direct to the washer 1 or is preferably used for dissolving the drained product from the still-dehydrator 12 by passing through the pipe 24 to the mixer 23.

The composition by weight of the reaction mixture contained in the still-dehydrator, which depends upon the speed of dehydration and the amount of drainage effected at 22, amounts, on the average, throughout the test to about 4.75% of maleic acid, about 14.25% of fumaric acid, about 74% of maleic anhydride, about 2% of resinous residues and about 5% of sulfolane.

The drained product 22 is dissolved in mixer 23 under vacuum and the insoluble material (fumaric acid and residues) is separated on filter 27, the cake of which is washed with water coming through 28.

For the purpose of dissolution in mixer 23, use is preferably made of the aqueous solution of maleic acid coming from the recoveries effected in barometric washers 7 and 18. Through 29 and 3, there are thus recycled to the washer 1, 200 moles per hour of recovered acid (125 moles coming from the suspension of the drained product and 75 moles coming from barometric washers 7 and 18), plus the sulfolane.

The filter cake constitutes the loss suffered in the process of the present invention. This loss includes the maleic acid which has not been extracted from the filter cake by washing and the fumaric acid which was formed from the maleic acid in the course of the dehydration process. This loss amounts to 1.5%.

The advantages obtained according to the present invention through the addition of sulfolane are the same as those which were mentioned in Example 6, i.e. the suppression of the risk of clogging the installation and the maintenance of clean heat exchange surfaces.

We claim:

1. A process for the preparation of maleic anhydride by dehydration of maleic acid, which comprises heating maleic acid at a temperature of from about 100° to about 210° C under a pressure of about 30 to about 760 mm Hg in the presence of sulfolane.

2. The process according to claim 1, wherein the maleic acid used contains maleic anhydride.

3. The process according to claim 1, wherein the maleic acid used is solid or molten maleic acid.

4. The process according to claim 1, wherein the maleic acid used is aqueous maleic acid.

5. The process according to claim 1, wherein the maleic acid used contains in addition a solvent forming an azeotrope with water.

6. The process according to claim 5, wherein the solvent forming an azeotrope with water is xylene.

7. The process according to claim 1, wherein the heating is carried out at a temperature of from about 120° to about 200° C under a pressure of about 60 to about 200 mm Hg.

8. The process according to claim 1, wherein the weight of the sulfolane used as referred to the weight of maleic acid is at least 2%.

9. The process according to claim 8, wherein the weight of the sulfolane used as referred to the weight of maleic acid is at least 5%.

10. The process according to claim 8, wherein the weight of the sulfolane used as referred to the weight of maleic acid is at least 10%.

11. The process according to claim 1, wherein the preparation of maleic anhydride is carried out continuously.

* * * * *